United States Patent [19]

Bloch et al.

[11] 4,340,057

[45] Jul. 20, 1982

[54] RADIATION INDUCED GRAFT POLYMERIZATION

[75] Inventors: Daniel R. Bloch; Charles N. Odders; John R. Rogers, all of Racine, Wis.

[73] Assignee: S. C. Johnson & Son, Inc., Racine, Wis.

[21] Appl. No.: 219,669

[22] Filed: Dec. 24, 1980

[51] Int. Cl.³ .............................................. A61F 13/18
[52] U.S. Cl. ............................ 128/284; 204/159.12; 204/160.1; 427/44; 428/248; 428/255; 428/274; 428/290; 428/507; 428/508; 428/511; 428/913; 428/305.5; 428/319.7; 128/285; 128/287
[58] Field of Search ...................... 204/159.12, 160.1; 128/284, 285, 287, 296; 427/44; 260/17.4 CL; 428/290, 507, 913, 255, 274, 304, 508, 511, 913, 248

[56] References Cited

U.S. PATENT DOCUMENTS

| | | | |
|---|---|---|---|
| 3,188,165 | 6/1965 | Maget et al. | 204/159.13 |
| 3,247,133 | 4/1966 | Chen | 204/159.12 |
| 3,252,880 | 5/1966 | Chapiro et al. | 204/159.12 |
| 3,514,385 | 5/1970 | Maget et al. | 204/159.12 |
| 3,779,881 | 12/1973 | Sakurada et al. | 204/159.15 |
| 4,036,588 | 7/1977 | Williams | 260/17.4 CL |

OTHER PUBLICATIONS

Textile Chemist and Colorist, pp. 37-43, vol. 9, No. 1, Jan. 1977.
Journal of Polymer Science: Part C, No. 4, pp. 615-629 (1963).
American Dyestuff Reporter, Dec. 2, 1968.

*Primary Examiner*—James J. Bell

[57] ABSTRACT

An absorbent material is prepared by treating a substrate with an aqueous monomer dispersion of an acrylate salt and a cross-linking monomer and thereafter irradiating the treated substrate with high energy ionizing radiation to form a cage matrix of the polymer and monomer substrate. The absorbent material can be swelled with a solution containing a volatile additive to dispense said additive over a period of time.

21 Claims, No Drawings

RADIATION INDUCED GRAFT POLYMERIZATION

BACKGROUND OF THE INVENTION

The present invention relates to a method for preparing a moisture absorbent material and the resulting moisture absorbent product. In particular, it relates to radiation induced graft polymerization of substrates to provide highly swellable materials and conversion of such materials to swollen, additive-dispensing products.

In the past it has proven difficult to substantially enhance the moisture absorbing ability of substrates, while maintaining their structural integrity. Highly absorbent cellulosic substrates, for example, are required to meet the ever-increasing need for diapers, tampons, sanitary napkins, medical sponges, bandages, cloth wipes, and the like. Such substrates may be required to absorb over 100 times their weight of aqueous fluid. Further, in the consumer and medical fields the need for storage-stable, water-swellable matrices adapted to carry aqueous solutions of easily volatized additives is greatly expanding.

It has long been known that synthetic polymers can be made more hydrophilic by radiation induced graft polymerization. Fabrics and films formed from addition polymers have been disclosed in U.S. Pat. No. 3,188,165, as possible substrates for the electron beam grafting thereto of unsaturated carboxylic acids or their preformed organic salts, in a single operation. Cellulosic substrates are not disclosed. Cross-linking momomers were not utilized. The typical add-on (weight gain of grafted polymer for the substrate) was only from about 25 to 30 weight percent. For practical purposes this is insufficient to provide enhanced moisture absorption and wet strength required for materials which are to be used as diapers, tampons and the like.

It is believed that the low dose rates imparted by the early prior art radiation sources, such as the Van de Graff electron accelerator, conventional X-ray equipment and radioactive isotopes, as cobalt 60, simply were insufficient to initiate the requisite degree of free radical generation to form the engrafted polymer network required. For commercial and other purposes, it has also been desired to provide a grafting process by which a sample can be properly irradiated to cause formation of sufficient active sites on the substrate and polymerization of monomer at production line speeds, such that the irradiated material can be quickly and efficiently worked into the desired end product.

Graft polymerization of natural polymeric material, including cellulosic fibers, with acrylic acid monomer is disclosed in U.S. Pat. No. 3,514,385. Low add-on, on the order of 25%, is reported. Irradiation is at low dosage rates. No cross-linking monomers are employed. Acrylic acid grafted substrates are converted to the sodium salt form in a separate step; no direct grafting of acrylate salts is disclosed.

In U.S. Pat. No. 3,799,881 polyester fiber is impregnated with a solution of from 5 to 20% acrylate salt monomer and 80% to 95% cross-linking monomer and irradiated to graft the resulting polymer to the polyester substrate. The weight increase of grafted polymer is very low, on the order of only 2–10%. The resulting polyester product is merely a "coated" polyester fiber material. The results achieved in this patent for sodium methacrylate were comparable to those achieved for sodium acrylate. This is in direct contrast to the present invention, wherein it has been found that high add-on of methacrylate (on the order of 60% or more), is not possible by conventional radiation grafting. Also, at the high ratio of cross-linking agent to monomer employed in U.S. Pat. No. 3,799,881, the resulting graft polymer is not swellable and exhibits a very low water absorption compared to that desired by industry.

In U.S. Pat. No. 3,247,133 polyethylene film is irradiated by an electron beam in the presence of monomer to form an ion exchange membrane. Add-ons of monomer are less than half the amount required for the proper degree of absorbability needed for diapers, tampons and the like. Cross-linking agents are mentioned as optional ingredients and in amounts (20%) which would make the material too rigid for normal use. No acrylate salts are disclosed.

Cross-linked hydrophilic finishes for polyester, utilizing ethoxylated acrylate monomer irradiated with an electron-beam, is disclosed in a reprinted article, originally appearing on pages 37–43 of Vol. 9, No. 1, Jan. 1977, in *Textile Chemist and Colorist*, published by the American Association of Textile Chemists and Colorists. The add-on of cross-linked monomer was very low, less than only 17%, with retained water being on the order of only 4 times the weight of fabric. For practical purposes, the material should retain on the order of 50–100 times its weight of water.

A proposal to increase water absorption in cellulosic materials employing electron beam induced graft polymerization of acrylic acid is disclosed in U.S. Pat. No. 4,036,588. A post-decrystallization step of 2 hours duration was essential to achieve a high degree of water absorption. No acrylate salts were employed. No cross-linking agents were disclosed. The radiation dose rate was too low for practical purposes.

Radiation induced grafts of up to about 22% acrylic acid on nylon, have been thereafter converted to the sodium acrylate salt by after-treatment with sodium carbonate, Magat et al., *J. Polym. Sc.*, Part C, No. 4, pp. 615–629 (1963). No cross-linking agents were employed.

In the past it has also been reported that radiation was a disappointing tool for cross-linking types of processing, particularly in the case of cellulosics and other fibers which degrade rather than cross-link on irradiation, *Am. Dyestuff Reporter*, Dec. 2, 1968, pp. 91–100, (93). It was recognized by the art that graft polymerization, initiated by ionizing radiation, was unpredictable and that in each case the amount of radiation from a given source had to be empirically determined for the particular result sought, col. 3, lines 72–75, U.S. Pat. No. 3,252,880.

SUMMARY OF THE INVENTION

It is, accordingly, an object of this invention to provide a method for substantially enhancing the capacity of a material to absorb an aqueous fluid, yet retain its dimensional stability in the swollen state.

It is another object of this invention to provide a highly moisture absorbent material adapted to stably retain its swollen configuration under adverse conditions of pressure, temperature or humidity.

It is an additional object to provide a fluid swelled article capable of dispensing predetermined amounts volatile additives.

It is a further object of the invention to make available a continuous method for efficiently producing a highly absorbent graft-polymerized material utilizing a high energy ionizing radiation source.

The above and other objects are met in a method for preparing moisture swellable absorbent material by treating a substrate, capable of forming graft polymers with an acrylate salt under the influence of high energy ionizing radiation, with an aqueous monomer dispersion. The dispersion is formed from (i) sodium acrylate, potassium acrylate, lithium acrylate, ammonium acrylate or mixtures thereof, and (ii) a water-dispersible cross-linking monomer. The cross-linking monomer is employed in amounts from about 2 to 10% by weight of the acrylate salt. The aqueous monomer dispersion has sufficient acrylate salt and cross-linking monomer solids to form a reaction product with the substrate in amounts from about 60 to 200% by weight of the substrate. Unless otherwise noted, all percentages are by weight.

The treated substrate carrying the acrylate and cross-linking monomers is then irradiated to form a graft polymer upon and within said substrate. The graft polymer is present both on the surface of the substrate and as an interpenetrating network within the substrate interstices. The graft polymer is also engrafted to the substrate. The irradiation is carried out with high energy ionizing radiation having an energy of at least about 150,000 electron volts (eV). The radiation dosage applied to the substrate is from about 0.5 to 25 megarads (mrads). The dose rate employed is no greater than about 90 megarads per second.

Cellulosic absorbent material is a preferred substrate for forming radiation grafted material. Such material is particularly useful for processing into diapers, tampons, bandages and the like. The radiation grafted absorbent material can be treated or swollen with an aqueous solution or dispersion containing volatile additives, such as a perfume, air freshener and disinfectant, to provide a dispensing matrix for the additive, which slowly volatilizes from the matrix.

The advantages of the present invention are legion. The irradiated material, inter alia, is highly moisture absorbent as compared to the untreated substrate. The degree of absorbency is based, in part, on the identity and porosity of the substrate utilized, the nature and amount of monomers employed, and the radiation conditions. For a non-woven cellulosic substrate, for example, the physical properties of the irradiated graft polymerized material compare favorably to the untreated substrate. In general, the irradiated material exhibits increased hand and slightly reduced physical strength, as compared to the untreated substrate due to the effect of radiation on the fibers. Other advantages are realized.

For example, dependent upon such factors as the degree of cross-linking and the quantity of water available, sheets, which are formed from cellulosic material treated in accordance with the process of the invention, can absorb on the order of 150 times their weight in water, while maintaining remarkable swollen dimensional stability. Under such circumstances, the material can be expected to swell up to about 100 times its original thickness. The swollen articles, however, exhibit sufficient stability to enzymes and acids found in urine, for example, to be employed as a diaper material.

It has been found that the wickability or rate of liquid adsorption by capillary action of radiation grafted cellulosic material is somewhat slower than the original untreated material. This property is valuable when the material is employed as a diaper, tampon, bandage or the like, since the fluid to be absorbed, as urine or blood, tends to remain in a more confined area for a longer period of time. Clothing in contact with the opposite side of the treated material is thereby better protected from contact with undesired fluid. Further, the treated cellulosic material, after being swollen with water, exhibits excellent liquid retention properties, even under the influence of elevated temperature and pressure. In addition the swollen material retains its stability, even after repeated freeze-thaw cycles. These properties are especially useful when the treated material is employed in articles, designed to absorb moisture or to dispense volatile agents. Further, the graft polymer tends to resist separation and sloughing from the substrate even under adverse conditions.

In general, the graft-polymerized material of the invention (after electron irradiation), is dry and ready for immediate fabrication into the desired article. No de-crystallization or other exotic treatment steps apart from a simple washing step to remove unreacted starting material or unattached polymer, is generally required. The substrate selected can be irradiated in any convenient industrial form, such as sheet form, batt form, scrim form, tow form, fabric form and the like.

DETAILED DESCRIPTION OF THE INVENTION

Substrates which are capable of forming graft polymers with an acrylate salt under the influence of high energy ionizing radiation are known in the art as "trunk polymers". Such trunk polymers form free radical sites or "active sites" on their skeleton, to which the polymerized acrylate and cross-linking monomer, attach. Suitable substrates include natural and synthetic polymeric materials, such as wool, leather, polyvinyl chloride, polyamides, polystyrene, polyesters, polyethers, polyurethanes, polyisobutylene, polypropylene, and the like, including their copolymers and graft polymers.

Best results are achieved when a porous substrate is employed, which is adapted to absorb and/or entrap the aqueous monomer dispersion of the invention. Accordingly, cellulosic substrates are preferred, such as woven- or non-woven cotton and woven or non-woven rayon, regenerated cellulose, paper, and non-woven cellulose sheets.

The substrate to be grafted is wetted or swollen by the aqueous monomer dispersion of the acrylate salt and the cross-linking monomer. Excess monomer dispersion is removed beyond that required to form the desired product, employing conventional means, such as padding rollers. As employed herein the term "dispersion" is intended to include dispersions and solutions.

The acrylate salt of the dispersion is a Group IA metal acrylate, particularly sodium acrylate, potassium acrylate or lithium acrylate; and ammonium acrylate or mixtures thereof. Minor amounts of other polymerizable monomers such as vinyl pyrrolidone, acrylamide, acrylonitrile, vinyl acetate and acrylic esters may be substituted for a portion of the acrylate salt, if desired.

When methacrylic acid or its salts are employed in place of the acrylate monomer, it has been found that insufficient quantities thereof are grafted to the substrate to provide satisfactory water absorption. When acrylic acid is substituted for the acrylate salt, without the use of cross-linking monomers, it has not proven possible to engraft sufficient amounts to provide acceptable water absorption, while maintaining a stable configuration for the swollen material upon use. When acrylic acid is employed together with a cross-linking monomer, the resulting material lacks swellability, sufficient for the purposes of this invention.

When Group IIA metal acrylates such as barium acrylate are employed in place of Group IA metal acrylates, then the resulting material likewise lacks sufficient absorbability for the purposes of the invention.

The cross-linking monomer is a water-dispersible polyfunctional compound susceptible to free radical initiation under ionizing irradiation. The cross-linker aids in linking the acrylate homopolymer strands to each other and to the substrate to form a graft polymer both on the surface of the substrate and within the substrate as an interpenetrating network. By increasing or decreasing the quantity of acrylate chains engrafted to the substrate and to each other, the cross-linking monomer controls the properties of the absorbent material in its swollen state.

Effective cross-linking monomers include vinyl phosphonate, a phosphate polymer with pendent vinyl groups; other phosphorous containing vinyls, such as alkyl, aryl and aralkyl phosphonates; di- tri-, tetra- and pentacrylates such as aluminum triacrylate, bisphenol A bis(2-hydroxypropyl) acrylate, 1,3-butanediol, diacrylate, 1,4-butanediol diacrylate, 2-butene-1,4-diol diacrylate, 1,10-decanediol diacrylate, diethyleneglycol diacrylate, dipentaerythritol monohydroxy pentaacrylate, ethoxylated bisphenol A diacrylate, ethylene glycol diacrylate, ferric triacrylate, 1,6-hexanediol diacrylate, 1,2,6-hexanetriol diacrylate, neopentyl glycol diacrylate, pentaerythritol tetraacrylate, pentaerythritol triacrylate, polyethylene glycol diacrylate, polypropylene glycol triacrylate, 1,3-propanediol diacrylate, propoxylated bisphenol C diacrylate, tetraethylene glycol diacrylate, triethylene glycol diacrylate, trimethylolethane triacrylate, trimethylol propane triacrylate, tripropylene glycol diacrylate, triacrylate of tris (2-hydroxyethyl) isocyanurate, and the corresponding methacrylates. Compounds with vinylic and allylic functionality can also be employed, such as vinylic alcohols, vinyl ketones, vinyl esters and vinyl ethers; examples of which include allyl alcohol, vinyl salicylate, allyl glycidyl ether, methyl vinyl ketone and the like.

In general, sufficient cross-linking monomer is utilized to ensure a stable material, after swelling. Instability of liquid-swollen material, which can result in sloughing of the material, results from insufficient bonding between the strands of the acrylate polymer, both to themselves, and to the substrate. Accordingly, at least about 2% by weight of cross-linking monomer is employed, based on the weight of the acrylate salt.

If excess cross-linking agent is employed, the graft polymer forms a tight interpenetrating network, which is highly rigid and inflexible, such that the material cannot swell sufficiently to entrap and absorb enough water for the purposes of this invention. In general, no greater than about 10% by weight of cross-linking monomer is employed, based on the weight of acrylate salt. Best results are obtained, and accordingly it is preferred, to employ from about 4 to 10% by weight of cross-linker, based on the acrylate salt.

After irradiation, the resulting graft polymer matrix of acrylate - cross-linker - substrate may be described as a unique cage matrix adapted to entrap and absorb liquids. This cage matrix of interpenetrating strands of polymerized monomer dispersion engrafted to the trunk polymer is unusually stable upon swelling with fluids.

The aqueous dispersion of acrylate salt and cross-linker contains up to about 70% by weight of solids depending upon the particular acrylate system selected. For most purposes the useful solids content is from about 40% to 70% by weight. The particular solids selected will vary depending upon the intended use of the material and the desired degree of add-on.

Sufficient monomer dispersion solids are employed to form a reaction product attached to the substrate in amounts from about 60% to 200% and preferably from about 75% to 200% by weight of substrate. The particular amount of added-on reaction product selected will depend, in part, on the identity of the acrylate salt, the desired end use of the material and the identity of the substrate. It has been found that the degree of add-on is in direct proportion to the concentration of the acrylate for any given set of radiation conditions. For many applications, the weight ratio of monomer dispersion to substrate is preferably about 40:60 to 80:20 and especially 65:35.

To form the monomer dispersion, the cross-linking monomer is usually dissolved or emulsified in an aqueous acrylate solution. If the cross-linker is not water soluble, it may be added to the acrylate solution in an emulsified form, employing conventional surfactants for emulsification. Also, a cosolvent system, such as a water-miscible organic solvent and water, may be employed to dissolve or disperse the cross-linker prior to addition. If need be, a surfactant may be employed in the system to assist in forming a uniform dispersion.

The pH of the monomer dispersion can vary somewhat from neutrality. The dispersion is most stable when the pH is slightly acidic.

After the substrate is treated with the aqueous monomer dispersion, it is subjected to irradiation with high energy ionizing radiation to form a graft polymer on the surface of, and an interpenetrating network within, the substrate. The substrate and attached network polymer, together form a cage structure or matrix.

Ionizing radiation, as the term is employed herein, includes gamma rays, beta rays, neutrons, accelerated electrons and heavy particles, such as X-rays, or mixtures of such, of sufficient intensity to fracture covalent bonds to generate free radicals on the trunk polymer (substrate), the acrylate monomer and the cross-linking monomer. The type of ionizing radiation selected, its intensity, the dose rate and total dose employed, depend, in part, upon the properties which the resulting graft polymer is intended to possess, and the nature of the substrate to be irradiated.

Enhanced processability, absorbability and stability have been obtained for the irradiated material employing electron beam irradiation. Accordingly, electron beam processing is preferred as the source for the high energy ionizing radiation.

Radiation generated from an electron beam accelerator or processor may be varied, dependent upon the voltage differential within the electron gun. The processor is adjusted to produce electrons of appropriate voltage to meet processing requirements. The extent to which high energy electrons penetrate a monomer-treated substrate of the invention depends upon their voltage at impact and the ability of the treated substrate to stop them. In general, the higher the voltage, the greater the electron beam penetration. If the electrons do not penetrate sufficiently, reaction initiation will not take place uniformly within the monomer-treated substrate. If the electrons penetrate excessively, they can pass through the substrate (i) generating little, if any, active sites or (ii) providing ineffective initiation in comparison to the total number of electrons available. If the treated substrate is sufficiently dense, it is often desirable to irradiate from both sides of the substrate with complementary amounts of energy.

The energy level selected is preferably that which will permit the electrons to deposit their energy in an efficient manner within the substrate. As the density of the treated substrate is varied by changing the loading of dispersion on substrate in accordance with the desired end uses, the energy level of the beam will be appropriately adjusted to obtain proper penetration.

In order to obtain satisfactory electron penetration into the substrate, ionizing radiation of at least about 150,000 electron volts (150 KeV) must be employed. Preferred swellable material with superior water absorption and dimensional stability properties has been produced, when the ionizing radiation energy is from about 200,000 to 300,000 eV and the dose rate is no greater than about 90 mrads/sec and preferably from about 2 to 45 megarads per second.

The amount of radiation actually absorbed by the treated substrate is the dose. Dose is measured in rads (radiation absorbed dose). One rad of radiation is equal to the absorption of 100 ergs of energy per gram of absorbing material. One megarad is $10^6$ rads. One megarad of radiation is equal to $1 \times 10^6$ amp. sec./cm².

The greater the dose, the more energy imparted to the treated substrate and the more likely that reaction will be initiated by generation of active sites via free radical formation. Some substrates are more innately reactive than others and require a smaller dose to initiate the graft polymerization. For best results the dose employed is a balance between that required to initiate the graft polymerization and that causing excessive degradation and decomposition of the substrate. The appropriate dose is, therefore, a function of (i) the reactivity of the aqueous monomer dispersion, (ii) the degree to which the substrate is predisposed to grafting and (iii) the amount of substrate to be irradiated.

The dosage employed for the present process is at least about 0.5 megarad and no greater than about 25 megarads. At a dosage less than about 0.5 megarads, there is insufficient initiation to provide a high add-on of engrafted polymer. It is preferred to employ a dosage of at least about 1.75 megarads, since enhanced add-on is thereby facilitated. At a dosage over about 25 megarads and on the order of about 30 megarads there is excess degradation of the substrate including a cellulosic substrate.

In radiation processing apparatus the dose is conveniently determined in accordance with the following equation:

$$\text{dose} = \frac{\text{current density}}{\text{exposure time}} \cdot Cm;$$

wherein the current density is in milliamperes, the exposure time is the sample exposure time and Cm is the processing machine constant (an inherent value depending upon the particular machine employed). Exposure time is often expressed in line speed.

The rate at which radiation is delivered to the treated substrate is the dose rate. An electron beam of a given energy can be delivered slowly or rapidly to provide the same total dose. A substrate that exhibits low reactivity at a given total dose may exhibit satisfactory reactivity at the same total dose, but at a different dose rate.

In selecting irradiation parameters, normally the energy of the electron beam is selected and the dose rate is selected. The desired total dose is then obtained by controlling the speed with which the treated material is actually exposed to the beam; the line speed. At a given dose rate, the total dose applied is inversely proportional to the line speed of the treated substrate as it passes through the beam; the larger the desired total dose; the slower the substrate must pass the beam to permit sufficient time for the total dose to accumulate.

It has been discovered that as the dose rate increases, while the intensity and total dosage remain constant, the graft polymerization add-on reaction is less efficient. It is postulated that insufficient active sites on the substrate are produced. Conversely, as the dose rate decreases with beam intensity and total dosage held constant, the add-on reaction tends to go to completion. At lower dose rates, to achieve the proper total dose, the production speed of the process must accordingly, be reduced.

Therefore, to provide the highest add-on in the radiation treated material, the dose rate preferably should be no greater than about 45 megarads per second. At low line speeds, the dose rate can be substantially less than 1 megarad per second. For practical purposes, however, the dose rate is preferably greater than 0.7 mrad/sec and more preferably from about 2 to 45 mrads/sec.

At high dose rates and high applied voltages, in order to provide a sufficient absorbed dosage, it may be necessary to pass the monomer treated substrate repeatedly through an electron beam, even at low conveyor or line speeds. This process is known to the art as "festooning". It may also be advisable to irradiate the sample from opposing sides with a pair of radiation heads. The total dose received by the sample will be the sum of the dose received from each head.

Irradiation may be carried out in the presence of air. However, for best results, irradiation is conducted in the absence of oxygen. The radiation grafting step can be carried at a broad range of temperatures, with the preferred range being from about 20° to 30° C. At this range of ambient temperatures, the heating or cooling energy requirements of the process are minimized. The use of chain transfer agents in the aqueous dispersion generally reduces the swellability of the absorbent material and may not be desirable.

The process of the invention may be applied to improve absorption of substrates in various forms such as webs, sheets, pads, yarns, batts, tows, creped tissue, cord, scrim, continuous fiber, floc, bristle, artificial straw, filament, fluff or fabric. The absorbent material of the process may be processed into a diaper, tampon, sanitary napkin, medical sponge, bandage, wiping cloth, soil mulch, disposable feminine hygiene shield and the like, in accordance with conventional procedures. For example, a disposable shield for garment protection can be formed from the absorbent material of the invention in accordance with U.S. Pat. No. 4,059,114.

A swelled article capable of dispensing predetermined amounts of volatile additives can be prepared by forming the moisture swellable absorbent material of the invention and thereafter treating said material with an aqueous solution or dispersion containing the volatile additive to permit the material to absorb the solution or dispersion. The volatile additive may be a perfume, an air freshening additive, a disinfectant, or the like. Sheets or batts of the absorbant material can be swelled with an aqueous solution of the volatile additive. Thereafter the swollen sheets can be fabricated into facial wipes, air fresheners, bandages or the like. If need be, the volatile additive can be emulsified in the solution, using conventional means.

To prepare the absorbent material of the invention the substrate to be radiation grafted is thoroughly wetted or swollen by an aqueous dispersion of the acrylate monomer and cross-linking monomer. The wetted or swollen substrate is passed through padding rollers or the like, to remove excess solution and to deposit the desired concentration of monomers on the substrate. The monomer treated substrate is thereafter irradiated with the desired amount of ionizing radiation, employing, for example, an electron beam from an electron processor, to initiate the grafting and polymerization reaction. Thereafter, if desired, the grafted absorbent material is washed with an aqueous solution to remove unattached polymer or unreacted monomer. Finally, the absorbent material is processed, as desired, to the appropriate end product.

Various embodiments of the process are possible. The untreated substrate may be presoaked in the monomer dispersion for a short time to permit a more through wetting of the substrate. The presoaking permits a more complete contact between the substrate and monomer solution. It also provides an opportunity for the substrate fibers to swell and to permit a deeper network of interpenetrating strands of cross-linked polymer to be engrafted.

The preferred electron beam irradiation-initiated graft polymerization provides substantial advantages over a chemically initiated reaction. Chemically initiated graft polymerization of the monomer dispersion is insufficient to provide the degree copolymer attachment to the substrate requisite for providing a swellable, dimensionally stable product which resists the destabilization effects of hot water and pressure.

Cellulosic substrates, particularly non-woven absorbent cotton or rayon, are especially suitable as the trunk polymer. Cellulosic substrates readily absorb the aqueous monomer dispersion in substantial quantities, which facilitates high add-on of polymer. After irradiation, cellulosic absorbent material is warm to the touch, and is easily processed into the final end product. The wickability of cellulosic substrates (or the rate by which the substrate absorbs water by capillary action) is substantially reduced after irradiation with the monomeric dispersion. This reduced wickability is highly desirable when the irradiated cellulosic material is employed as a diaper, tampon or bandage, since blood, urine of the like is better confined to the area in which it is originally deposited.

Other uses of the instant absorbent material or the material swollen with predetermined fluids will be apparent to those skilled in the art. For example, the grafted alkali salts can be used to ion exchange with calcium or magnesium ions to soften water.

The following examples illustrate certain preferred embodiments of the invention and are not limitative of scope.

EXAMPLE I

To illustrate the preparation of an absorbent material of the invention, 303 grams (5.4 moles) of potassium hydroxide pellets were dissolved in water and the resulting alkaline solution slowly added to 393 grams (5.4 moles) of acrylic acid with cooling. Next, to a solution of 5 grams of polyethoxylated octylphenol (40EO), a surfactant available under the trademark, Triton X-405 (70% solids) and 25 grams of distilled water, there was added 70 grams of trimethylolpropane triacrylate, with agitation. Agitation was continued until a creamy white, water-out emulsion was formed.

To 1,000 grams of the potassium acrylate solution (60% solids) there was added 45 grams of the triacrylate emulsion. The resulting aqueous monomer dispersion was agitated to uniformity. The monomer dispersion was 61% solids and the weight ratio of acrylate monomer to cross-linking monomer was 95:5.

A 12 inch square of non-woven cloth of rayon viscose, available under the trademark, F1468-14 from Stearns and Foster, was submerged in and thoroughly wetted by, the aqueous monomer dispersion. The wetted cloth was passed between rollers to remove excess solution from the cloth.

An electron processor identified as Model No. CB 250/30/20 sold by Energy Sciences Inc., having a machine constant of 30, was adjusted to deliver 250 KeV electrons at 5mA. A sample conveyor belt was set at a line speed of 30 ft./min. such that the sample cloth received 5 mrads of radiation. The sample cloth was passed through the radiation chamber of the processor twice, with each side of the sample being exposed once, for a total dose of 10 mrads delivered to the sample.

The grafted absorbent sample sheet was washed in water to remove unattached polymer or unreacted monomer. The resulting absorbent sheets, after drying, were ready for processing into a desired end product.

EXAMPLE 2

In order to illustrate preparation of a swelled article adapted to deliver a volatile additive, a dried sheet sample was prepared according to Example I. A volatile additive emulsion was prepared by mixing 1.6 grams of dioctyl sodium sulfosuccinate, sold as Aerosol OT-75% active solids, 3 grams of lemon perfume and 120 grams of distilled water.

The Aerosol-OT was dissolved in the distilled water. The perfume was then added under high agitation until a creamy, white emulsion was formed. Thereafter, one quarter of the absorbent sample, prepared according to Example 1, was placed in the emulsion and absorbed the entire emulsion. The perfumed swollen sheet was useful as an air freshener.

EXAMPLE 3

Irradiation conditions were evaluated to determine their effect on the amount of graft polymer added-on to a substrate as follows:

Samples of non-woven rayon fabric were impregnated with an aqueous dispersion of sodium acrylate and a vinyl phosphonate cross-linking agent, sold under the trademark, FYROL 76 by Stauffer Chemicals, in accordance with the procedure illustrated in Example 1. The treated samples were irradiated with an electron beam from commercially-available electron processors. The processor employed to irradiate Samples 1–10 had a machine constant of about 24 (250 KeV max. model from Radiation Polymer Co.). The processor utilized to irradiate Samples 11–14 had a machine constant of 18 (250 KeV max, model from Energy Sciences Inc. The processor utilized to irradiate Samples 15 and 16 was a High Voltage Engineering unit having a maximum output voltage of 500 KeV. The beam voltage, line speed, current density and total radiation dosage were measured and tabulated in Table 1 hereunder. The weight proportions of the acrylate and cross-linking monomer aqueous dispersions are provided. The reactions went to completion. Accordingly the add-ons to the samples were equivalent to the amount of monomer dispersion applied to the substrates.

The irradiated samples were washed and dried. The weight of added graft polymer was determined by subtracting the final weight of the irradiated sample from the initial weight of the untreated sample. The % Add-On represents the weight increase of the untreated sample divided by the total weight of the irradiated sample multiplied by 100%.

ethylene glycol diacrylate, are substituted for the cross-linking monomers employed.

EXAMPLE 5

A sample of paper towel was impregnated with a monomer dispersion of 98 parts sodium acrylate per 2 parts vinyl phosphonate cross-linking monomer in accordance with the procedure of Example 1 and irradiated at a dosage of 16.6 Mrads under irradiation conditions similar to those of Example 1. The add-on was measured at 75.63%.

TABLE 1

IRRADIATION CONDITIONS

| Sample No. | Monomer Solution | Total Dose in Mrads | Beam Voltage in KeV | Beam Current Density in Milliamps | Line Speed in ft./min. | % Add-On |
|---|---|---|---|---|---|---|
| 1 | **96NaA/4VP | 5.2 | 250 | 2 | 9 | 90.26 |
| 2 | 96NaA/4VP*** | 6.0 | 250 | 2 | 8 | 94.02 |
| 3 | 96NaA/4VP | 6.9 | 250 | 2 | 7 | 94.74 |
| 4 | 96NaA/4VP | 5.2 | 250 | 2 | 9 | 94.37 |
| 5 | 96NaA/4VP | 5.0 | 250 | 5 | 24 | 89.80 |
| 6 | 96NaA/4VP | 5.0 | 250 | 8 | 38 | 91.79 |
| 7 | 96NaA/4VP | 5.0 | 250 | 10 | 48 | 90.98 |
| 8 | 96NaA/4VP | 5.2 | 200 | 2 | 9 | 92.91 |
| 9 | 96NaA/4VP | 6.1 | 200 | 2 | 8 | 94.18 |
| 10 | 96NaA/4VP | 7.1 | 200 | 2 | 7 | 97.04 |
| 11 | 96NaA/4VP | *(2)x 5 | 175 | 2.5 | 9 | 84.07 |
| 12 | 96NaA/4VP | *(2)x 5 | 200 | 2.5 | 9 | 84.48 |
| 13 | 96NaA/4VP | *(2)x 5 | 175 | 14 | 51 | 73.01 |
| 14 | 96NaA/4VP | *(2)x 5 | 200 | 14 | 51 | 75.17 |
| 15 | 95NaA/5VP | *(2)x 4.6 | 300 | 0.5 | — | 76.64 |
| 16 | ****95KaA/5VP | 4.8 | 300 | 2 | — | 84.14 |

*(2)x in the table means that each side of the substrate received the indicated dose in mrads.
**NaA is sodium acrylate monomer.
***VP is vinyl phosphonate cross-linking monomer sold as Fyrol 76.
****KA is potassium acrylate monomer.

The test results illustrate the enhanced add-on obtained when the total dose is between about 5 and 10 mrads and the beam voltage is at least about 150,000 KeV.

When similar tests were conducted on samples irradiated at 11, 13, and 16 Mrads employing a monomer dispersion of 98NaA/2VP, the add-ons were 78.5%, 75% and 75.6%, respectively.

EXAMPLE 4

The effects of varying the nature and quantity of the cross-linking monomer are illustrated in Table 2, below. Samples of monomer dispersion treated rayon were prepared in accordance with the procedure of Example 1 and irradiated. The add-on for each sample was determined.

A sample of spun bonded polypropylene fabric was impregnated with a monomer dispersion and irradiated as in Example 1. A polymeric add-on of 66.56% was achieved. The degree of grafting of the polymer to the substrate was not determined. The monomer solution employed was 98 parts sodium acrylate per 2 parts vinyl phosphonate. The total dose of radiation was 7.0 Mrads and the beam energy supplied was 250 KeV at 10mA.

EXAMPLE 6

The absorbency of the graft polymerized materials of the invention is illustrated in the following tests in which a series of 16 samples of polymer-grafted nonwoven rayon fabric was prepared in accordance with the conditions set forth in the following Table 3. Table 3 presents the weight ratio of grams deionized water

TABLE 2

RADIATION CONDITIONS

| Sample No. | Monomer Solution | Dose/ Mrads | Line Speed ft./min. | Beam Power KeV | Beam Output mA | % Graft Polymer |
|---|---|---|---|---|---|---|
| A | 96NaA/4VP | 5 | 48 | 250 | 10 | 88.54 |
| B | 95NaA/5VP | *(2)x 4.6 | 2.6 | 250 | 0.5 | 76.64 |
| C | 92NaA/8VP | 5 | 48 | 250 | 10 | 87.50 |
| D | 96NaA/4TMPTA** | 5 | 48 | 250 | 10 | 87.04 |
| E | 92NaA/8TMPTA | 5 | 48 | 250 | 10 | 87.10 |

*(2)x signifies that each side of the sample was irradiated with the indicated dose.
**TMPTA is trimethyol propane triacrylate.

Similar results are obtained, when other cross-linking monomers, such as pentaerythritol tracrylate and tetraabsorbed per gram of polymer grafted fabric, when the irradiated samples were totally immersed in water and allowed to reach swelling equilibrium.

TABLE 3

| Sample No. | Monomer Solution | IRRADIATION CONDITIONS ||||  gm. water absorbed gm. grafted fabric |
|---|---|---|---|---|---|---|
| | | Dose Mrads | Line Speed ft/min | Beam Power KeV | Beam Output mA | |
| 1 | 96NaA/4TMPTA | 5 | 10 | 175 | 2.5 | 157 |
| 2 | 96NaA/4TMPTA | 5 | 10 | 175 | 2.5 | 178 |
| 3 | 96NaA/4VP | (2)x 5 | 51 | 200 | 14 | 58 |
| 4 | 96NaA/4VP | (2)x 5 | 51 | 200 | 14 | 49 |
| 5 | 96NaA/4VP | (2)x 5 | 10 | 200 | 2.5 | 46 |
| 6 | 96NaA/4VP | (2)x 5 | 10 | 200 | 2.5 | 44 |
| 7 | 96NaA/4VP | (2)x 5 | 10 | 200 | 2.5 | 40 |
| 8 | 96NaA/4TMPTA | 10 | 10 | 200 | 2.5 | 120 |
| 9 | 96NaA/4TMPTA | 10 | 10 | 200 | 2.5 | 145 |
| 10 | 96NaA/4TMPTA | 5 | 10 | 175 | 2.5 | 166 |
| 11 | 96NaA/4TMPTA | 5 | 10 | 175 | 2.5 | 182 |
| 12 | 96NaA/4VP | (2)x 5 | 51 | 200 | 14 | 68 |
| 13 | 96NaA/4TMPTA | 5 | 10 | 200 | 2.5 | 104 |
| 14 | 96NaA/4TMPTA | (2)x 5 | 51 | 200 | 14 | 88 |
| 15 | 96NaA/4TMPTA | (2)x 5 | 51 | 200 | 14 | 86 |

NaA, (2)x, VP and TMPTA have the same significance as set forth in Tables 1 and 2 hereinbefore.

In contrast to the high absorbency values obtained in this series of tests, two untreated control samples of nonwoven rayon exhibited a water absorbency of only 7.5 grams/gram. and 6.0 grams/gram, respectively.

Another well recognized measure of absorbency is the capacity of a sample to absorb saline solution. Accordingly, samples of polymer-grafted fabric were also tested for saline solution absorbency by totally immersing the samples in a 0.9% NaCl solution and allowing them to reach a swollen equilibrium.

For the samples tested, the saline solution absorbability was from 20.97 to 44.10 grams saline solution absorbed per gram of fabric. Untreated fabric employed as a control typically provided saline absorbability of 7.5 and 6.0 gms. per gm. fabric.

In addition, the samples were also tested for their capacity to absorb synthetic urine comprising a solution of 97.09% deionized water, 1.94% urea, 0.80% NaCl, 0.11% $MgSO_4 \cdot H_2O$ and 0.06% $CaCl_2$.

The absorbency of the grafted samples for synthetic urine was from 6.55 to 39.09 gms/gm. The very high capacity of the absorbent material of the invention to swell with liquids such as water, saline solution and synthetic urine solution, together with the dimensional stability of the swelled material and the low wickability thereof, offer definite advantages over many commercially available "super" absorbent materials.

Other modifications of the invention will be apparent to those of ordinary skill in the art. This invention is not to be limited, except as set forth in the following claims:

What is claimed is:

1. Method of preparing moisture-swellable absorbent material comprising:
   (a) treating a substrate capable of forming graft polymers with an acrylate salt under the influence of high energy ionizing radiation, with an aqueous monomer dispersion of
      (i) an acrylate salt selected from the group consisting of sodium acrylate, potassium acrylate, lithium acrylate, ammonium acrylate and mixtures thereof, and;
      (ii) a water-dispersible cross-linking monomer in amounts from about 2 percent to 10 percent by weight of said acrylate salt, said aqueous dispersion having sufficient acrylate salt and cross-linking monomer to form a reaction product with said substrate in amounts from about 60 percent to 200 percent by weight of the substrate; and
   (b) irradiating said treated substrate with high energy ionizing radition having an energy of at least about 150,000 electron volts at a dose rate no greater than 90 megarads per second to provide a dosage from about 0.5 to 25 megarads, to thereby form a graft polymer on the surface of, and on interpenetrating network within, said substrate.

2. The process of claim 1, wherein said material is a web, sheet, pad, yarn, batt, tow, creped tissue, cord, scrim, continuous fiber, floc, bristle, artificial straw, filament, fluff, or fabric.

3. The process of claim 1 wherein said material is a cellulosic absorbent material.

4. The process of claim 3, wherein said material is cotton, rayon, a cellulose derivative or a regenerated cellulose.

5. The process of claim 4, wherein said material is a nonwoven absorbent article.

6. The process of claim 5, wherein said article is a diaper, tampon, sanitary napkin, medical sponge, bandage, wiping cloth, soil mulch or disposable feminine hygiene shield.

7. The process of claim 1, wherein the water dispersible cross-linking monomer is selected from the group consisting of pentaerythritol triacrylate, tetraethylene glycol diacrylate, trimethylol propane triacrylate, a vinyl phosphonate and mixtures thereof.

8. The process of claim 1 wherein the cross-linking monomer is employed in amounts of about 4 to 10 percent by weight of said acrylate salt.

9. The process of claim 1, wherein the monomer solids in the aqueous dispersion is from about 40 to 70 percent by weight.

10. The process of claim 1, wherein the high energy ionizing radiation is an electron beam.

11. The process of claim 1, wherein said aqueous dispersion comprises sodium acrylate and from about 4 to 8 percent by weight of said acrylate, of a vinyl phosphonate monomer.

12. The process of claim 1 wherein said reaction product add-on to said substrate is from about 75% to 200% by weight and said irradiating step is conducted at a dose rate no greater than 45 megarads per second to provide a dosage from about 1.75 to 25 megarads.

13. The moisture-swellable absorbent material formed by the process which comprises:

(a) treating a substrate capable of forming graft polymers with an acrylate salt under the influence of high energy ionizing radiation with an aqueous monomer dispersion of
  (i) an acrylate salt selected from the group consisting of sodium acrylate, potassium acrylate, lithium acrylate, ammonium acrylate and mixtures thereof, and;
  (ii) a water-dispersible cross-linking monomer in amounts from about 2% to 10% by weight of said acrylate salt in said aqueous dispersion having sufficient acrylate salt and cross-linking monomer to form a reaction product with said substrate in amounts from about 60 percent to 200 percent by weight of substrate,
(b) by irradiating said treated substrate with high energy ionizing radiation having an energy of at least about 150,000 electron volts at a dose rate up to about 90 megarads per second to provide a dosage from about 0.5 to 25 megarads to thereby form a graft polymer on the surface and an interpenetrating network within, said substrate.

14. The product of claim 13, wherein said material is a cellulosic non-woven absorbent article.

15. The product of claim 14, wherein the article is a diaper.

16. The product of claim 13 wherein said reaction product add-on to said substrate is from about 75% to 200% by weight and said irradiating step is conducted at a dose rate no greater than 45 megarads per second to provide a dosage from about 1.75 to 25 megarads.

17. A method for preparing a swelled article capable of dispensing volatile additives which comprises forming a moisture swellable absorbent material by:
  (a) treating substrate capable of forming graft polymers with an acrylate salt under the influence of high energy ionizing radiation, with an aqueous monomer dispersion of
    (i) an acrylate salt selected from the group consisting of sodium acrylate, potassium acrylate, lithium acrylate, ammonium acrylate and mixtures thereof, and;
    (ii) a water-dispersible cross-linking monomer in amounts from about 2 to 10 percent by weight of said acrylate salt, said aqueous dispersion having sufficient acrylate salt and cross-linking monomer to form a reaction product with said substrate in amounts from about 60 percent to 200 percent by weight of the substrate;
  (b) irradiating said treated substrate with high energy ionizing radiation having an energy of at least about 150,000 electron volts at a dose rate no greater than about 90 megarads per second to provide a dosage from 0.5 to 25 megarads and thereby form a graft polymer on the surface of, and an interpenetrating network within, said substrate, and
  (c) treating said swellable material with an aqueous solution or dispersion containing said volatile additive to permit said material to absorb said aqueous solution or dispersion.

18. The method of claim 17 wherein said reaction product add-on to said substrate is from about 75% to 200% by weight and said irradiating step is conducted at a dose rate no greater than 45 megarads per second to provide a dosage from about 1.75 to 25 megarads.

19. A swelled article capable of dispensing predetermined amounts of volatile additive formed by the process which comprises forming a moisture swellable absorbent material by:
  (a) treating substrate capable of forming graft polymers with an acrylate salt under the influence of high energy ionizing radiation, with an aqueous monomer dispersion of
    (i) an acrylate salt selected from the group consisting of sodium acrylate, potassium acrylate, lithium acrylate, ammonium acrylate and mixtures thereof, and;
    (ii) a water-dispersible cross-linking monomer in amounts from about 2 to 10 percent by weight of said acrylate salt, said aqueous dispersion having sufficient acrylate salt and cross-linking monomer to form a reaction product with said substrate in amounts from about 60 percent to 200 percent by weight of the substrate;
  (b) irradiating said treated substrate with high energy ionizing radiation having an energy of at least about 150,000 electron volts at a dose rate no greater than about 90 megarads per second to provide a dosage from 0.5 to 25 megarads and thereby form a graft polymer on the surface, and in an interpenetrating network within, said substrate, and
  (c) treating said swellable material with an aqueous solution or dispersion containing said volatile additive to permit said material to absorb said aqueous solution or dispersion.

20. The article of claim 19, wherein said additive is a perfume, an air freshener, a disinfectant, or mixtures thereof.

21. The article of claim 19, wherein said reaction product add-on to said substrate is from about 75% to 200% by weight and said irradiating step is conducted at a dose rate no greater than 45 megarads per second to provide a dosage from about 1.75 to 25 megarads.

* * * * *